United States Patent [19]

Berg

[11] Patent Number: 5,007,940

[45] Date of Patent: Apr. 16, 1991

[54] INJECTABLE POLYMERIC BODIES

[75] Inventor: Eric P. Berg, Plymouth, Minn.

[73] Assignee: American Medical Systems, Inc., Minnetonka, Minn.

[21] Appl. No.: 364,722

[22] Filed: Jun. 9, 1989

[51] Int. Cl.$^5$ .......................... A61F 2/02; A61F 2/12; A61M 5/00
[52] U.S. Cl. ......................................... 623/66; 623/8; 623/11; 600/30; 424/423; 523/113
[58] Field of Search ............... 623/8, 11, 16; 523/113; 424/423, 400, 78, 81; 600/30

[56] References Cited

U.S. PATENT DOCUMENTS

| | | | |
|---|---|---|---|
| 4,527,293 | 7/1985 | Eckstein et al. | 424/423 X |
| 4,631,188 | 12/1986 | Stoy et al. | |
| 4,686,962 | 8/1987 | Haber | |
| 4,773,393 | 9/1988 | Haber | 600/30 |
| 4,803,075 | 2/1989 | Wallace et al. | 424/423 |

OTHER PUBLICATIONS

Kaufman et al., "Transurethral PTFE Injection", (1984), Journal of Urology, vol. 132, pp. 463–464.
Stoy, "New Type of Hydrogel for Controlled Drug Delivery", (1989), Journal of Biomaterials Applications, vol. 3, pp. 552–604.

*Primary Examiner*—Alan W. Cannon
*Attorney, Agent, or Firm*—Peter C. Richardson; Lawrence C. Akers; Mark Dryer

[57] ABSTRACT

An injectable composition comprising a plurality of discrete physiologically-compatible, non-biodegradable, polymeric bodies, said bodies having (i) an average outside diameter of from about 0.005 to 0.20 inch, (ii) reversible deformability of about 20 to 75% of their unstressed outside diameter, and (iii) a lubricious surface; a process for the preparation of said composition and a method for treating a tissue condition in a patient using said composition.

7 Claims, No Drawings

INJECTABLE POLYMERIC BODIES

BACKGROUND OF THE INVENTION

This invention relates to an injectable composition comprising polymeric bodies, particularly deformable hydrogel macrodisks. The invention is also concerned with a process for preparing said composition and to a method for treating a tissue condition, particularly for tissue augmentation, by injecting said composition into the site of said condition.

The use of various injectable or inflatable polymeric bodies for tissue augmentation and prosthetic implants is known in the art. For example, U.S. Pat. No. 4,686,962 discloses an assembly for hypodermically implanting a genitourinary prosthesis for the treatment of urinary incontinence which includes an inflatable containment membrane which is inflated by material injected with a hypodermic needle.

Urinary incontinence also has been treated by the transurethral injection of polytetrafluoroethylene (PTFE), usually in the form of a paste or encapsulated particles. See, for example, "Transurethral Polytetrafluoroethylene Injection for Post-prostatectomy Urinary Incontinence" by M. Kaufman et al, the *Journal of Urology*, Vol. 132, September 1984, p. 463–464, and the references cited therein. However, if the particles are small, complications arise from undesirable migration or removal by phagocytes causing potential problematical accumulation at other sites, for example the brain, kidney or lungs.

Another application for tissue augmentation is in the treatment of a hypoplastic breast wherein a typical prior art prosthesis is provided by a silicone membrane enveloping a suitable bulking material, for example a saline solution or a flexible polysiloxane gel. One disadvantage of the saline-containing prosthesis is that microleaks in the silicone membrane or valving mechanism lead to deflation of the prosthesis. A problem with polysiloxane gel is that it contains low-molecular weight compounds, such as cyclic oligomers, which slowly migrate into the patient's system and cause problems similar to those associated with the PTFE particles discussed above.

A solution to the problems associated with earlier polymeric implants is provided by U.S. Pat. No. 4,631,188, which discloses a method of in situ formation of a solid polymer in a mammal which comprises injecting into said mammal a physiologically-acceptable polymeric composition comprising a solution in a water-soluble, non-toxic polar solvent of a water-insoluble, non-toxic, non-cross-linked polymer or copolymer selected from polymers and copolymers of acrylonitrile or vinylacetate, linear or slightly branched polymers and copolymers of 2-hydroxyethylacetate and methacrylate, poly-(N-vinyliminocarbonyl), polycondensates and polyadducts and having a solubility parameter of from about 9.2 to about 15.5 $(cal/cc)^{\frac{1}{2}}$.

The water-insoluble non-toxic polymers used in the method disclosed in U.S. Pat. No. 4,631,188 fall within the class of compounds known in the art as water-swellable hydrogels and the disclosure in said patent relating to this class of compounds is incorporated herein by reference. As noted in the patent, water-swellable hydrogels have been used in the art for tissue augmentation, usually in implants of defined shape and size. The method disclosed in the patent overcomes problems associated with such preformed implants by injecting a solution of said hydrogel into a mammal resulting in the in situ formation of a solid polymer in the mammal. This method involves the use of a water-soluble polar solvent, for example dimethyl sulfoxide (DMSO), which, although non-toxic, is an unnecessary adjunct to the implant and has to be dispersed by the mammal's metabolism. Furthermore, since the polymer is water-insoluble but water-swellable, formation of the solid polymer is dependent upon the amount of water present in the mammalian tissue and the size and shape of the implant is difficult to control.

Surprisingly, it has now been found that an injectable composition based upon a water-insoluble, non-toxic hydrogel but not containing undesirable solvents may be provided if the hydrogel is in the form of discrete, deformable bodies as hereinafter described. Moreover, the discrete, deformable bodies, since they already contain their full complement of water, retain their individual identity and are stable after injection so that the size and shape of the implant does not alter.

SUMMARY OF THE INVENTION

In accordance with the present invention there is provided an injectable composition consisting of a plurality of discrete physiologically-compatible, non-biodegradable, polymeric bodies, said bodies having (i) an average outside diameter of from about 0.005 to 0.20 inch, (ii) reversible deformability of about 20 to 75% of their unstressed outside diameter, and (iii) a lubricious surface.

The invention also provides a process for the preparation of an injectable composition as described above which comprises dissolving a physiologically-compatible, non-biodegradable, water-insoluble, non-cross-linked polymer in a dipolar, aprotic organic solvent, rapidly injecting the resulting solution in a fine stream into a relatively large volume of a liquid medium which is a non-solvent for the polymer while slowly stirring said medium so that discrete bodies of the polymer are formed, washing said bodies until said solvent is removed and recovering bodies of the desired size by filtration through an appropriate sieve.

The invention further provides a method for treating a tissue condition in a patient which comprises injecting into the tissue site a tissue enhancing amount of an injectable composition comprising a plurality of discrete, physiologically-compatible, non-biodegradable, polymeric bodies having (i) an average outside diameter of from about 0.005 to 0.20 inch, (ii) reversible deformability of about 20 to 75% of their unstressed outside diameter and (iii) a lubricious surface.

DETAILED DESCRIPTION OF THE INVENTION

The injectable composition of the invention consists of discrete bodies of a particular size and possessing unique characteristics which enable them to be injectable, i.e. to be introduced into and contained within a hypodermic needle, without the aid of a carrier or solvent. Thus the injectable composition may not be in the form of a traditional solution, suspension or paste, but merely may comprise a plurality of the above-described discrete bodies themselves. The injectability of the bodies is particularly surprising because in many instances the average size of the bodies is greater than the inside diameter of the needle in which they are to be used. Thus, as more particularly described hereinafter, when the bodies are in the preferred form of macrodisks, the average outside diameter of the macrodisks may be up to about three times the inside diameter of a hypodermic needle through which they may be successfully passed without undergoing observable damage.

The unique and surprising injectability of the discrete bodies which form the composition of the invention may be attributed primarily to the characteristics which are defined herein as reversible deformability and lubricious surface.

As used herein the term "reversible deformability" means that the bodies are sufficiently flexible to be deformed into virtually any shape by folding, compression or both when subjected to the physical stress required to produce the relevant deformation, for example the deformation required to introduce the bodies into a hypodermic needle, but return to their original shape and size when said stress is removed, e.g. when they are expressed from the needle.

It is also essential that each discrete body has a lubricious surface, i.e. said surface must be sufficiently smooth and slippery so that the bodies do not stick to any surface with which they come into contact during the performance of the invention, for example, the inside surface of a hypodermic needle, nor do they stick to themselves. The fact that the bodies do not stick to themselves means that they slip with respect to each other and, when injected, can be contoured or manipulated into any desired shape and subsequently retain their discrete identity and do not form undesirable lumps or agglomerates.

Preferably, the discrete polymeric bodies are made from a water-swellable hydrogel and a particularly preferred hydrogel is a partially hydrolyzed polyacrylonitrile. This material, when used to prepare bodies by the process according to the invention, provides bodies having the required reversible deformability and lubricious surface described above.

The lubricity of the bodies may be even further enhanced if the bodies include a water-soluble polysaccharide, such as dextran.

The discrete polymeric bodies present in the composition of the invention have an average outside diameter of from about 0.005 to 0.20 inch. Thus they are large enough to avoid undesirable migration from the site of injection, which was serious problem with the microparticles, for example PTFE, used in the prior art. However, because of the deformability characteristic described hereinabove, they are still small enough to be injectable without undergoing irreversible damage.

In a particularly preferred embodiment of the invention the bodies are deformable macrodisks having an average outside diameter of from about 0.01 to 0.085 inch. Macrodisks having an average diameter at the upper end of the stated range, with a few even as large as 0.10 inch in diameter, may be injected through an 18 ga needle (internal diameter 0.034 inch) with no apparent macrodisk damage.

In an alternative embodiment, the bodies may be spherical bodies having an average outside diameter of from about 0.01 to 0.085 inch. However, with this embodiment, the bodies are less deformable than the macrodisks and the diameter of the needle has to be relatively larger for a similar diameter body.

The unique discrete, deformable and slippery bodies which provide the injectable composition of the invention are prepared by a process which comprises dissolving a physiologically-compatible, non-biodegradeable, water-insoluble, non-crosslinked polymer, preferably a water-swellable hydrogel, in a dipolar aprotic organic solvent, for example dimethyl sulfoxide (DMSO), dimethylformamide or N,N-dimethylacetamide, rapidly injecting the resulting solution in a fine stream, for example through a hypodermic needle, into a relatively large volume of a liquid medium which is a non-solvent for the polymer while slowly stirring said medium so that discrete bodies of the polymer are formed. When the fine stream of solution hits the non-solvent liquid medium the polymer, e.g. hydrogel, forms small bodies and the stirring of the liquid medium prevents these bodies from agglomerating together. Under these conditions it appears that a membrane or hydrogel/liquid interface forms on the surface of each individual body, the solvent, e.g. DMSO, is expressed from the body leaving a discrete solid body which does not stick to or agglomerate with any adjacent body. The bodies thus formed are then washed, preferably with water or, alternatively with the same non-solvent used in their preparation, to remove all the solvent; and the washed discrete bodies are then recovered by filtration through an appropriate sieve.

In the above described process the non-solvent liquid medium is preferably water, usually distilled water. Other suitable liquids are acetone, low molecular weight alcohols, for example, methanol, ethanol or isopropanol, or mixtures of these liquids with water. Generally, when the non-solvent is water the hydrogel bodies assume the form of flat disks with rounded edges, referred to herein as macrodisks, and these macrodisks generally have an average outside diameter of from about 0.01 to 0.085 inch. When the non-solvent is acetone there is a tendency for the bodies to form spheres.

When the bodies are washed and recovered they may be stored in a suitable sterile non-solvent liquid, for example, saline solution.

The injectable composition of the invention is particularly suitable for the treatment of a number of tissue conditions in mammals, particularly humans. The expression "tissue conditions" as used herein is intended to be generic to any situation or condition which requires augmentation, enhancement, medication, strengthening or replacement of tissue, and includes, but is not limited to: tissue augmentation of a hypoplastic breast; transurethral and periurethral injection to treat urinary incontinence; tissue augmentation of scar tissue; and treatment of tissue deficiency arising from severe wounds, e.g. "plastic surgery".

According to the invention the aforesaid tissue conditions are treated by a method which comprises injecting into the tissue site a tissue enhancing amount of an injectable composition comprising a plurality of discrete physiologically-compatible, non-biodegradable, polymeric bodies having (i) an average outside diameter of from about 0.005 to 0.20 inch, preferably from about 0.01 to 0.085 inch, (ii) reversible deformability of about 20 to 75% of their unstressed outside diameter and (iii) a lubricious surface.

To perform the method, the bodies preferably are injected into the tissue through a hypodermic needle of about 25 ga to 14 ga. The gauge of the needle used will depend upon the size (outside diameter) of the bodies in the composition. Thus, when the bodies are macrodisks having an average outside diameter of about 0.082 inch they will pass through a needle of 18 ga (about 0.034 inch internal diameter) with no apparent damage.

A preferred embodiment of the method according to the invention comprises augmentation of a hypoplastic breast either (i) by directly injecting into the breast, or (ii) by making an incision in the breast to form a pocket therein and injecting into said pocket, a tissue-augmentation amount of an injectable composition as described above. The discrete bodies in the composition are preferably deformable macrodisks of a water-swellable hydrogel, preferably a partially hydrolyzed polyacrylonitrile having an average molecular weight of from about 100,000 to 150,000, said macrodisks having an average outside diameter of from about 0.01 to 0.085 inch. The size of the macrodisks prevents undesirable migration to other parts of the patient's body and the lubricity of the macrodisks allows for manipulation of the injected composition into the desired shape for the prosthesis and affords a tissue-like softness upon manual compression. Since the hydrogel is non-biodegradable, the prosthesis retains its integrity indefinitely.

A modification of the above embodiment comprises placing in said pocket in the patient's breast a physiologically-compatible inflatable polymeric shell, preferably made from a silicone polymer or polyurethane, and inflating said shell with a tissue-augmentation amount of an injectable composition according to the invention. In this embodiment either the shell may be placed in the pocket and inflated in situ by injecting the composition thereinto or the prosthesis may be preformed by inflating the shell with a desired amount of the composition and the preformed prosthesis then placed in the pocket.

In a further embodiment of the invention, urinary incontinence may be treated by a method which comprises urethral tissue augmentation by injecting the above described injectable composition into the patient's urethra.

A still further embodiment of the invention is a method for the treatment of a tissue condition arising from a wound which produces a tissue deficiency or a scar which comprises augmenting said deficiency by an appropriate amount of an injectable composition as described above and contouring the site if necessary.

The invention will be more particularly described with reference to the following Examples which illustrate various embodiments of the invention.

EXAMPLE 1

This Example illustrates a typical procedure for preparing injectable discrete macrodisks from partially hydrolyzed polyacrylonitrile (PHPA).

20 gms. of ground PHPA were added to a beaker containing 180 gms. of DMSO and the mixture stirred at a temperature of 70° C. until the polymer was dissolved. The warm solution was vacuum filtered (5$\mu$) and then rapidly injected through a 25 ga needle into a container containing 2.0 liters of distilled water. The water was slowly stirred to ensure singulation of the macrodisks. After the macrodisks were formed they are repeatedly washed with distilled water until substantially all the DMSO was removed. The resulting macrodisks were collected by filtration from water and sieved through a 10 mesh polypropylene screen and collected on an 18 mesh screen. The resulting macrodisks had an average outside diameter of 0.082 inch, although disks as small as 0.050 inch and as large as 0.10 inch were also present in small quantities. The overall yield was approximately 70% by weight.

EXAMPLE 2

Macrodisks as prepared in Example 1 were steam sterilized in a sealed 20 ml. glass vial containing 30% w/w distilled water. The sterilized macrodisks were placed into a 3 cc. plastic syringe and, using only moderate finger pressure, were injected through an 18 ga needle with no apparent macrodisk damage.

EXAMPLE 3

Macrodisks as prepared in Example 1 were mixed with 30% w/w of a 25% (w/w) dextran (Sigma, clinical grade, MW 77,800) aqueous solution. After steam sterilization in a sealed 20 ml. glass vial, the macrodisks were placed in a 3 cc. plastic syringe and the material was expressed with only moderate finger pressure through an 18 ga needle. The presence of dextran, due to its lubrication effect, facilitated injection compared to Example 2.

EXAMPLE 4

Macrodisks as prepared in Example 1 were placed in a 3 cc. plastic syringe and steam sterilized in the presence of 30% w/w distilled water as carrier. Varying amounts of the composition (0.20-1.0 cc.) were injected subcutaneously in New Zealand white rabbits through an 18 ga needle. Injection site biopsies were taken at one week, one month, and three months. Tissue reactions were very mild with a thin, well-defined continuous collagenous capsule observed around the implant material after one month. No evidence of macrodisk migration away from the injection site was observed histologically.

EXAMPLE 5

A solution containing 10% w/w of PHPA in DMSO was rapidly injected through a 25 ga needle into 250 ml. of slowly stirred acetone. The resulting spherical bodies were separated and screened as in Example 1. The spheres were equilibrated in distilled water, suspended in dextran as described in Example 3, and sterilized in a capped glass vial. The spheres were placed into 1 ml. and 3 ml. plastic syringes and passed through a 15 ga needle using moderate finger pressure.

EXAMPLE 6

A comparison of PHPA macrodisks and spheres was made to determine what size of each would pass through various constricting orifices under moderate finger pressure without undergoing observable damage. The results are given in the following Table:

TABLE

| Sample Type | Maximum Sample Diameter (inch) | Minimum Needle I.D. (inch) |
|---|---|---|
| PHPA Macrodisk | 0.100 | 0.034 (18ga) |
| PHPA Sphere | 0.075 | 0.054 (15ga) |

The above results indicate that macrodisks and spheres according to the present invention compress and deform during injection to effectively reduce their outside diameter to pass through an injection needle of lesser inside diameter than the outside diameter of the macrodisk or sphere. The outside diameter of the macrodisks may be as much as about three times the inside diameter of the needle, while the diameter of the spheres may be up to about one and a half times the inside diameter of the needle.

I claim:

1. An injectable composition consisting of plurality of discrete physiologically-compatible, non-biodegradable, polymeric bodies, said bodies having (i) an average outside diameter of from about 0.005 to 0.20 inch, (ii) reversible deformability of about 20 to 75% of their unstressed outside diameter, and (iii) a lubricious surface.

2. A composition according to claim 1, in which said bodies are made from a water-swellable hydrogel.

3. A composition according to claim 2, in which said bodies also include a water-soluble polysaccharide.

4. A composition according to claim 2, in which said hydrogel is a partially hydrolyzed polyacrylonitrile.

5. A composition according to claim 3, in which said bodies are made from a mixture of a partially hydrolyzed polyacrylonitrile and dextran.

6. A composition according to claim 1, in which said bodies are deformable macrodisks having an average outside diameter of from about 0.01 to 0.085 inch.

7. A composition according to claim 1, in which said bodies are spherical bodies having an average outside diameter of from about 0.01 to 0.085 inch.

* * * * *